(12) United States Patent
Geibel et al.

(10) Patent No.: US 8,785,656 B2
(45) Date of Patent: Jul. 22, 2014

(54) TELESCOPING SYNTHESIS OF 5-AMINO-4-NITROSO-1-ALKYL-1H-PYRAZOLE SALT

(71) Applicant: The Procter & Gamble Company, Cincinnati, OH (US)

(72) Inventors: Wolfram Geibel, Huenfeld (DE); Ingo Weber, Gruenstadt (DE); Armin Osan, Bebra (DE); Markus Speckbacher, Mettenheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/768,519

(22) Filed: Feb. 15, 2013

(65) Prior Publication Data

US 2013/0217891 A1  Aug. 22, 2013

(30) Foreign Application Priority Data

Feb. 16, 2012 (EP) ..................... 12155707

(51) Int. Cl.
*C07D 231/10* (2006.01)
(52) U.S. Cl.
CPC ................... *C07D 231/10* (2013.01)
USPC .................... 548/371.4; 548/372.1
(58) Field of Classification Search
CPC ...................................... C07D 231/10
USPC .......................... 548/371.4, 372.1
See application file for complete search history.

(56) References Cited

U.S. PATENT DOCUMENTS

| | | |
|---|---|---|
| 3,709,437 A | 1/1973 | Wright |
| 3,937,364 A | 2/1976 | Wright |
| 4,022,351 A | 5/1977 | Wright |
| 4,147,306 A | 4/1979 | Bennett |
| 4,184,615 A | 1/1980 | Wright |
| 4,615,467 A | 10/1986 | Grogan |
| 5,061,289 A | 10/1991 | Clausen |
| 5,380,340 A | 1/1995 | Neunhoeffer |
| 5,430,159 A | 7/1995 | Neunhoeffer |
| 5,443,569 A | 8/1995 | Uehira |
| 5,534,267 A | 7/1996 | Neunhoeffer |
| 5,663,366 A | 9/1997 | Neunhoeffer |
| 5,718,731 A | 2/1998 | Loewe |
| 5,752,983 A | 5/1998 | Audousset |
| 5,766,576 A | 6/1998 | Loewe |
| 5,769,902 A | 6/1998 | Samain |
| 5,785,717 A | 7/1998 | Maubru |
| 5,865,855 A | 2/1999 | Doehling |
| 5,931,973 A | 8/1999 | Malle |
| 6,053,364 A | 4/2000 | Van der Heijden |
| 6,090,162 A | 7/2000 | Maubru |
| 6,099,592 A | 8/2000 | Vidal |
| 6,118,008 A | 9/2000 | Malle |
| 6,338,741 B1 | 1/2002 | Vidal |
| 6,379,396 B1 | 4/2002 | Audousset |
| 6,452,019 B1 | 9/2002 | Cook |
| 6,503,282 B1 | 1/2003 | Braun |
| 6,554,871 B2 | 4/2003 | Braun |
| 6,600,050 B2 | 7/2003 | Chassot |
| 6,604,693 B2 | 8/2003 | Santagiuliana |
| 6,645,258 B2 | 11/2003 | Vidal |
| 6,660,046 B1 | 12/2003 | Terranova |
| 6,716,257 B2 | 4/2004 | Goettel |
| 6,740,127 B2 | 5/2004 | Friess |

(Continued)

FOREIGN PATENT DOCUMENTS

| | | |
|---|---|---|
| CA | 2646867 A1 | 3/2009 |
| DE | 3432983 A1 | 4/1985 |

(Continued)

OTHER PUBLICATIONS

[Database Registry Chemical Abstracts Service, Columbus, Ohio, Accession No. RN 1248707-36-9, Entered STN: Oct. 29, 2010].*

(Continued)

*Primary Examiner* — Samantha Shterengarts
(74) *Attorney, Agent, or Firm* — James T. Fondriest

(57) ABSTRACT

A telescoping synthesis of 5-amino-4-nitroso-1-alkyl-1H-pyrazole salt derivatives of formula (I), the compound (I) itself, and its use as an intermediate in the fabrication of 1-alkyl-4,5-diaminopyrazole salts of general formula (IX). The compounds of formula (IX) can be used as precursor dyes in oxidative hair dye compositions.

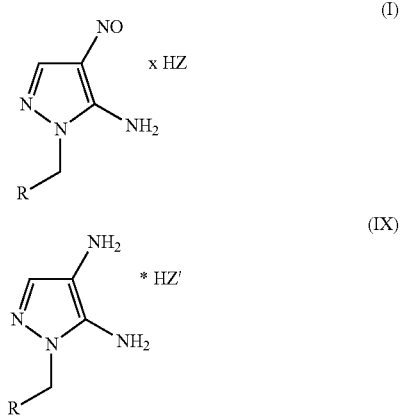

R is a mono- or poly-substituted or unsubstituted, straight or branched, saturated or mono- or poly-unsaturated, alkyl group. HZ and HZ' are organic or mineral acids.

10 Claims, 2 Drawing Sheets

(56) References Cited

U.S. PATENT DOCUMENTS

| | | |
|---|---|---|
| 6,780,203 B1 | 8/2004 | Maubru |
| 6,793,687 B2 | 9/2004 | Javet |
| 6,855,827 B2 | 2/2005 | Vidal |
| 6,887,280 B2 | 5/2005 | Lim |
| 6,905,522 B2 | 6/2005 | Kravtchenko |
| 6,939,382 B2 | 9/2005 | Fessmann |
| 7,004,979 B2 | 2/2006 | Kravtchenko |
| 7,014,663 B2 | 3/2006 | Fessmann |
| 7,018,426 B2 | 3/2006 | Javet |
| 7,056,354 B2 | 6/2006 | Fessmann |
| 7,070,629 B2 | 7/2006 | Kravtchenko |
| 7,091,350 B2 | 8/2006 | Fessmann |
| 7,153,330 B2 | 12/2006 | Cotteret |
| 7,195,649 B2 | 3/2007 | Goettel |
| 7,250,063 B2 | 7/2007 | Fessmann |
| 7,285,136 B2 | 10/2007 | Fessmann |
| 7,285,137 B2 | 10/2007 | Vidal |
| 7,300,469 B2 | 11/2007 | Fessmann |
| 7,927,381 B2 | 4/2011 | Hercouet |
| 2003/0000027 A1 | 1/2003 | Hoeffkes |
| 2003/0106167 A1 | 6/2003 | Rose |
| 2004/0216242 A1 | 11/2004 | Kravtchenko |
| 2006/0183781 A1 | 8/2006 | Goettel |
| 2006/0219738 A1 | 10/2006 | Izuka |
| 2007/0033742 A1 | 2/2007 | Goettel |
| 2007/0037987 A1 | 2/2007 | Chamberlin |
| 2007/0050924 A1 | 3/2007 | Cotteret |
| 2008/0141468 A1 | 6/2008 | Cotteret |
| 2013/0212810 A1 | 8/2013 | Geibel |

FOREIGN PATENT DOCUMENTS

| | | |
|---|---|---|
| DE | 19619112 A1 | 11/1997 |
| DE | 10032135 A1 | 1/2002 |
| DE | 20017640 U1 | 2/2002 |
| EP | 0663204 A1 | 7/1995 |
| EP | 0873109 B1 | 2/2004 |
| EP | 1405628 A1 | 4/2004 |
| EP | 1488783 B1 | 11/2006 |
| EP | 1787631 A1 | 5/2007 |
| EP | 1787632 A1 | 5/2007 |
| EP | 1795178 A2 | 6/2007 |
| EP | 1795179 A1 | 6/2007 |
| EP | 1797863 A1 | 6/2007 |
| EP | 1985282 A2 | 10/2008 |
| FR | 2604622 B1 | 12/1990 |
| FR | 2831055 B1 | 5/2004 |
| WO | WO0147475 A2 | 7/2001 |
| WO | WO0209662 A2 | 2/2002 |
| WO | WO02055500 A1 | 7/2002 |
| WO | WO02083090 A2 | 10/2002 |
| WO | WO2004024109 A1 | 3/2004 |
| WO | WO2005023209 A1 | 3/2005 |
| WO | WO2008047210 A2 | 4/2008 |
| WO | WO2009077390 A2 | 6/2009 |

OTHER PUBLICATIONS

Hans Höhn; XP-002681362; journal "Zeitschrift für Chemie", 10(10), 386-8; 1970.

* cited by examiner

TELESCOPING SYNTHESIS OF 5-AMINO-4-NITROSO-1-ALKYL-1H-PYRAZOLE SALT

FIELD OF THE INVENTION

The present invention relates to a telescoping synthesis of 5-amino-4-nitroso-1-alkyl-1H-pyrazole salt derivative of formula (I), the compound (I) itself, and its use as an intermediate in the fabrication of 1-alkyl-4,5-diaminopyrazole salts of general formula (IX). The compounds of formula (IX) can be used as precursor dyes in oxidative hair dye compositions.

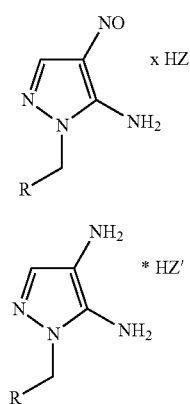

R is a mono- or poly-substituted or unsubstituted, straight or branched, saturated or mono- or poly-unsaturated, alkyl group. HZ and HZ' are mineral or organic acids.

BACKGROUND OF THE INVENTION

Although scarce in nature, pyrazole, its derivatives and physiologically compatible salts have found uses in many areas, such as pharmaceuticals, agricultural chemicals and hair dyes. Since the discovery of the high potential of these pyrazole derivatives, many publications have been devoted to the synthesis of pyrazoles and related compounds.

In particular, in the oxidative hair dyeing field, 1-substituted-4,5-diaminopyrazole of general formula (II) and salts thereof have shown to be interesting primary intermediates, providing a wide pallet of colour when used with various couplers in the presence of an oxidative dyeing medium.

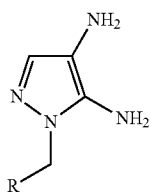

U.S. Pat. No. 6,452,019 discloses an improved process for the preparation of 4,5-diamino-1-(2'-hydroxyethyl)pyrazole and acid addition salts thereof such as the addition salt from sulfuric acid. The process comprises a combination of steps beginning with an alkyl(alkoxymethylene)cyanoacetate and 2-hydroxyethylhydrazine and the formation of intermediate compounds 5-amino-4-alkoxycarbonyl-1-(2'-hydroxyethyl) pyrazole, 5-amino-4-carboxyl-1-(2'-hydroxyethyl)pyrazole, 5-amino-1-(2'-hydroxyethyl)pyrazole, 5-amino-1-(2'-hydroxyethyl)-4-nitrosopyrazole.

U.S. Pat. No. 5,663,366 describes a process for making 4,5-diaminopyrazole derivative compounds of the formula (D):

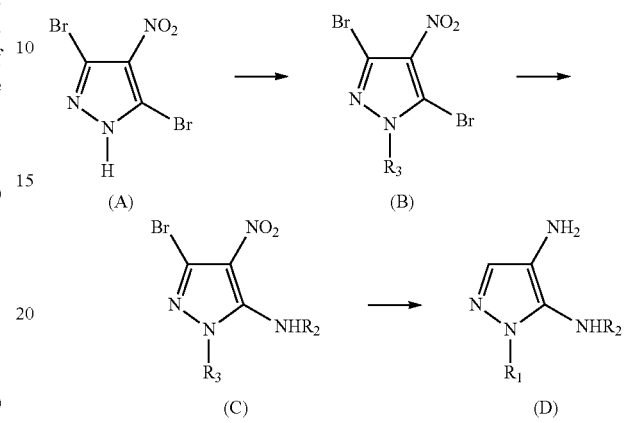

wherein $R_1$ and $R_2$ are independently selected from the group consisting of hydrogen, alkyl radicals having one to six carbon atoms and hydroxyalkyl radicals having two to four carbon atoms, provided that $R_2$ may not be tertiary butyl. In said process a) the 3,5-dibromo-4-nitropyrazole (A) is first alkylated in the 1-position by converting with C1- to C6-alkyl halides, C2- to C4-hydroxyalkyl halides or benzyl halides in dimethylformamide (DMF) (method I) or by converting with C1- to C6-alkyl sulfate, C2- to C4-hydroxyalkyl sulfate or benzyl sulfate and caustic solution (method II); b) in a subsequent step, the N-substituted 3,5-dibromo-4-nitropyrazoles of general formula (B) are heated in an aqueous, alcoholic or aqueous-alcoholic solution of C1- to C6-alkyl amine, C2- to C4-hydroxyalkyl amine or benzyl amine or in the corresponding amine itself, as solvent, at a temperature of 60° C. to 80° C.; and c) the compounds of general formula (C) are then hydrogenated using a palladium-on-activated-carbon catalyst with a palladium content of 10 percent by weight to produce compounds of general formula (D).

Hans Höhn describes a synthesis of pyrazole derivatives in the journal "Zeitschrift für Chemie", 10(10), 386-8; 1970.

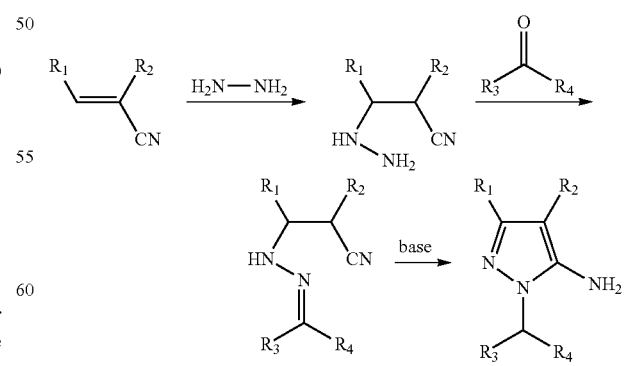

The present invention describes a new synthetic route to reach the 1-substituted-4,5-diaminopyrazole of general formula (II) via the key intermediate of the general formula (I).

In particular, the invention provides a sequential one-pot synthesis; with reagents added to a reactor one at a time and without work-up in between. Thus, the major advantage of the process provided by the present invention is to prevent the "workup"; i.e. the several manipulations usually required at the end of a chemical reaction, in order to isolate and purify the intermediates. In addition we can avoid contact with toxic intermediates such as hydrazine. Hydrazine itself and some alkyl- and phenyl-substituted derivatives are officially classified as carcinogens Carc IB (former class carc cat 2 under DSD) in Annex VI of the CLP regulation 1272/2008/EC. As a final step any un-reacted hydrazine can be degraded by an excess of the nitroso source present in the reaction mixture into nitrogen gas.

SUMMARY OF THE INVENTION

A new process has been developed to synthesize compounds of general formula (II), via a key intermediate of general formula (I), adduct of a telescoping one-pot synthesis. Thus, this allows the production of said compounds of general of formula (II), in a novel, high yield, cost effective and simple way. The telescoping process comprises the steps of:

(a) synthesizing the intermediate 3-hydrazinylpropanenitrile (IV) via a 1,4-Michael addition:

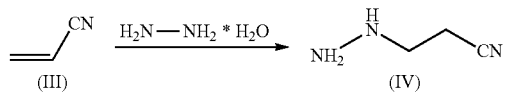

(b) synthesizing the intermediate 3-(2-alkylidenehydrazinyl)propanenitrile (VI) via a condensation:

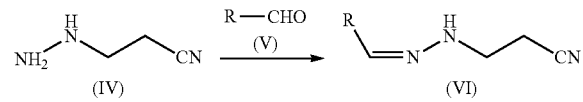

wherein R is a mono- or poly-substituted or unsubstituted, straight or branched, saturated or mono- or poly-unsaturated, alkyl system, (c) synthesizing the intermediate 5-amino-1-alkyl-1H-pyrazole (VII) via a cyclisation of (VI);

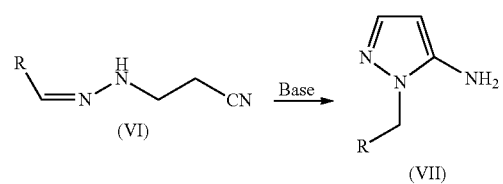

(d) synthesizing the intermediate 5-amino-4-nitroso-1-alkyl-1H-pyrazole salt (I) via a nitrosation;

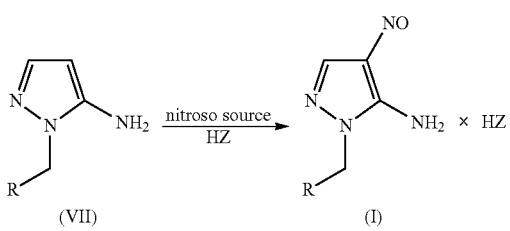

wherein R is a mono- or poly-substituted or unsubstituted, straight or branched, saturated or mono- or poly-unsaturated, alkyl or heteroalkyl group. More particularly R may be a $C_1$-$C_{11}$ straight unsubstituted alkyl group, in particular C3 to C7, especially pentyl.

The intermediate compound of formula (I) may be then further treated to form a salt of 4,5-amino-1-n-hexyl-1H-pyrazole of formula (IX). This and other aspects of the invention will now be further discussed in the following non-limiting detailed description.

DETAILED DESCRIPTION OF THE INVENTION

Definitions

Figure 1:
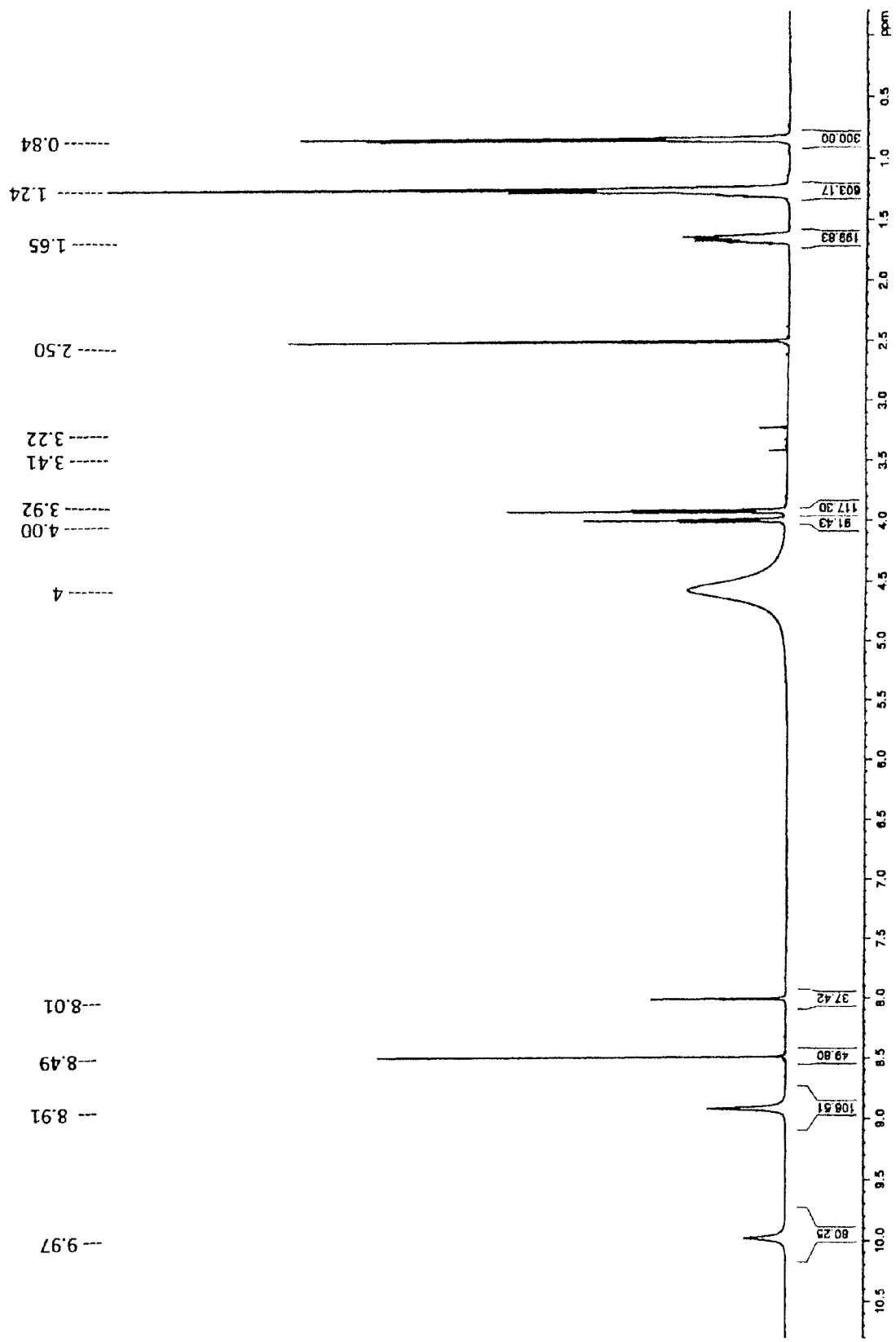
FIG. 1 is $^1$H NMR of 5-amino-4-nitroso-1-n-hexyl-1H-pyrazole HCl salt (herein I-a).

The different steps involved in the telescoping one-pot synthesis, and leading to the intermediates described will now be detailed. It is to be understood that within the scope of this invention, numerous potentially and actually tautomeric compounds are involved. It is to be understood that when this development refers to a particular structure, all of the reasonable additional tautomeric structures are included. In the art, tautomeric structures are frequently represented by one single structure and the invention follows this general practice.

The term "substituted" refers to a substituent selected from the group of $C_1$-$C_{12}$ straight or branched carbon chain, as well as halogen, methoxy-, ethoxy-, phosphorus, sulphurous or nitrogen derivated substituents.

It is to be understood that the steps described to make intermediate compound (I) are performed in a sequential one-pot synthesis, with reagents added to a reactor one at a time and without work-up in between. The reaction steps require suitable solvents, as is indicated below.

I. The First Step a) Consists of the Formation of the 3-hydrazinylpropanenitrile (IV) Via a 1,4 Michael Addition Using Acrylonitrile (III) and Hydrazine Hydrate (a) Synthesizing the Intermediate 3-hydrazinylpropanenitrile (IV)

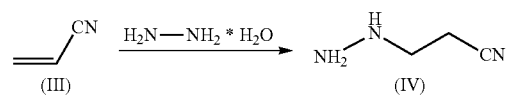

Non limiting examples of solvents for the step a) comprise pentane, 1,2-dimethoxyethane, cyclopentane, hexane, cyclohexane, benzene, toluene, 1,4-dioxane, chloroform, xylol, methyl-tert-butyl-ether, tert-butanol, dichloromethane, tetrahydrofuran, methyl-tetrahydrofuran, n-butanol, isopropanol, n-propanol, ethanol, methanol, water and mixtures thereof. In a preferred embodiment the solvent is n-propanol. Ionic liquids such as hexafluorophosphate salt of 1-butyl-3-methylimidazolium (BMIM) may also be used as solvents in the different reactions of the invention if applicable.

After the post reaction time, the obtained reaction mixture is immediately converted via step b) below without any work-up to isolate (IV).

II. The Second Step b) Consists of the Formation of the Intermediate 3-(2-alkylidenehydrazinyl)propanenitrile (VI) Via a Condensation with Intermediate (IV) and Aldehyde (V)

(b) Synthesizing the Intermediate 3-(2-alkylidenehydrazinyl)propanenitrile (VI)

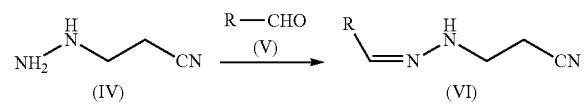

R is a mono- or poly-substituted or unsubstituted, straight or branched, saturated or mono- or poly-unsaturated, alkyl or heteroalkyl group. More particularly R may be a C1-C11 straight unsubstituted alkyl group, in particular C3 to C7, especially pentyl. The solvent for step b) may be the same solvent as the one used in step a).

After the second reaction step b) the condensation reaction is performed. The resulting water and the solvent can be removed using conventional methods such as distillation. An extra solvent (toluene for example) can also be added in order to create an azeotrope and improve the removal of water generated during the condensation step b).

Once the conversion of the intermediate (IV) into the intermediate (VI) is completed, the crude solvent free intermediate (VI) present in the reaction vessel is taken directly to the next step.

III. The Third Step c) Consists of the Formation of 5-amino-1-alkyl-1H-pyrazole (VII) Via a Cyclisation with Intermediate (VI) in the Presence of a Base (c) Synthesizing the Intermediate 5-amino-1-alkyl-1H-pyrazole (VII)

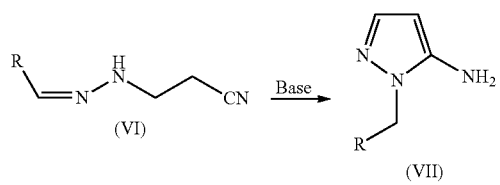

Non limiting examples of solvents for the step c) comprise 1,2-dimethoxyethane, pentane, cyclopentane, hexane, cyclohexane, benzene, toluene, 1,4-dioxane, diethyl ether, tetrahydrofuran, methyl-tetrahydrofuran, n-butanol, isopropanol, n-propanol, ethanol, methanol, water and mixtures thereof. In a preferred embodiment the solvent is selected from the group consisting of n-butanol, isopropanol, n-propanol, ethanol, methanol, more preferably n-propanol.

Non limiting examples of bases for the step c) comprise sodium methylate (=Sodium methoxide), potassium methylate, lithium methylate, sodium ethylate, potassium ethylate, lithium ethylate, sodium hydroxide, potassium hydroxide, ammonium hydroxide, calcium hydroxide, magnesium hydroxide, barium hydroxide, aluminum hydroxide, ferrous hydroxide or hydroxide, ferric hydroxide or Iron (III) hydroxide Zinc hydroxide, lithium hydroxide, sodium bicarbonate, alkali and earthalkali alcoholates as well as metal hydroxides such as sodium tert-butylate, potassium tert. butylate and mixtures thereof. In a preferred embodiment the preferred bases are selected from the group consisting of sodium methylate, potassium methylate and lithium methylate.

IV. The Fourth Step d) Consists of the Formation of Intermediate 5-amino-4-nitroso-1-alkyl-1H-pyrazole-salt (I) Via a Nitrosation Step of Intermediate (VII) in the Presence of an Acid (d) Synthesizing 5-amino-4-nitroso-1-alkyl-1H-pyrazole Salt (I)

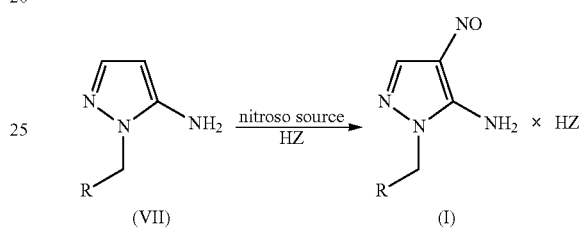

HZ may be chosen from any suitable mineral or organic acids. Non limiting examples of acid HZ for the step d) comprise HCl, $CF_3COOH$, $H_2SO_4$, $H_2SO_3$, $H_2CO_3$, $HNO_3$, $CH_3COOH$, $H_3PO_4$, and mixtures thereof. In a preferred embodiment the acid HZ is selected from the group consisting of HCl, $H_2SO_4$, $H_2SO_3$, more preferably HCl. Acid conditions are believed to be needed to produce the NO+-unit from the nitroso source, as is known in the art.

Non limiting examples of solvents for the step d) comprise 1,2-dimethoxyethane, pentane, cyclopentane, hexane, cyclohexane, benzene, toluene, 1,4-dioxane, diethyl ether, tetrahydrofuran, methyl-tetrahydrofuran, n-butanol, isopropanol, n-propanol, ethanol, methanol, water and mixtures thereof. In a preferred embodiment the solvent is preferably 1,2-dimethoxyethane.

Non limiting examples of nitroso source for the step d) comprise 3-methylbutyl nitrite, nitrosylsulfonic acid, tert-butylnitrite, butylnitrite, nitrite salts such sodium and potassium nitrite and mixtures thereof. In a preferred embodiment the nitroso source is preferably 3-methylbutyl nitrite.

After the last step of the sequence is performed, compound (I) precipitates upon its formation or by triturating the reaction mixture with an adequate solvent. Hence the reaction vessel, at the end of the telescoping one pot synthesis, comprises the un-reacted intermediate of formula (VII) soluble in the solvent and the desired compound of formula (I) as a precipitate. A simple filtration allows isolating the compound of formula (I) as a salt.

Non limiting examples of additional reactions that can be performed with the compound of formula (I) are described below. Indeed, once this sequence of reactions has been achieved successfully, the compound (I) can be converted to its free base, and followed by a conversion again to another salt, if desired.

V. The Fifth Step e) Consists of the Formation of the Intermediate 5-amino-4-nitros-1-alkyl-1H-pyrazole (VIII) Via a Basic Treatment with Intermediate (I) in the Presence of a Base (e) Synthesizing 5-amino-4-nitroso-1-alkyl-1H-pyrazole (VIII)

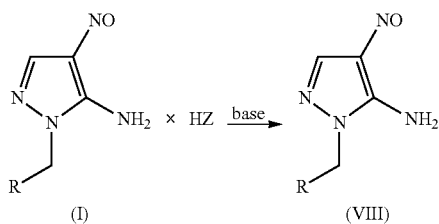

Non limiting examples of bases for the step e) comprise ammonia, alcoholates such as sodium methylate, potassium methylate, lithium methylate, alcali or earthalkali hydrxydes such as sodium hydroxide, potassium hydroxide, ammonium hydroxide, calcium hydroxide, magnesium hydroxide, barium hydroxide, aluminum hydroxide, ferrous hydroxide or Iron (II) hydroxide, ferric hydroxide or Iron (III) hydroxide, zinc hydroxide, lithium hydroxide, sodium bicarbonate, sodium acetate, potassium acetate, lithium acetate, ammonium acetate, sodium tert-butylate, potassium tert-butylate and mixtures thereof. The preferred base may be ammonia.

Non limiting examples of solvents for the step e) comprise pentane, 1,2-dimethoxyethane, cyclopentane, hexane, cyclohexane, benzene, toluene, 1,4-dioxane, diethyl ether, tetrahydrofuran, methyl-tetrahydrofuran, n-butanol, isopropanol, n-propanol, ethanol, methanol, water and mixtures thereof. In a preferred embodiment the solvent may be a mixture of water and methanol.

VI. The Sixth Step f) Consists of the Formation of 4,5-amino-1-alkyl-1H-pyrazole-HZ (IX) Starting with Intermediate (VIII) in the Presence of a Reducing Agent, Followed by Acid Treatment with an Acid HZ'

(f) Synthesizing 4,5-amino-1-alkyl-1H-pyrazole (IX)

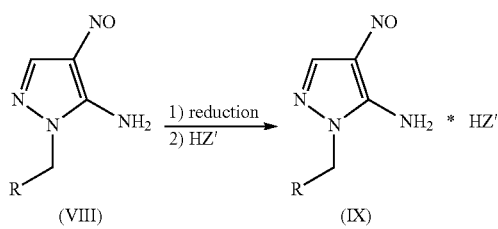

Non limiting examples of solvents for the step f) comprise pentane, 1,2-dimethoxyethane, cyclopentane, hexane, cyclohexane, benzene, toluene, 1,4-dioxane, diethyl ether, tetrahydrofuran, methyl-tetrahydrofuran, n-butanol, isopropanol, n-propanol, ethanol, methanol and mixtures thereof. In a preferred embodiment the solvent is selected from the group consisting of water and methanol.

Non limiting examples of a reducing agent for the step f) comprising hydrogen source such as Hydrazine, $H_2$ with a metal catalyst selected from the group consisting of Fe, Pd/C, Pd/(OH)$_2$, Raney-Ni, PtO$_2$ and mixtures thereof. In a preferred embodiment the reducing agent is a mixture of $H_2$ and Pd/C.

HZ' may be chosen from any suitable organic or mineral acid. Non limiting examples of acid HZ' for the step f) comprise HCl, $H_2SO_4$, $0.5H_2SO_4$, $H_3PO_4$, $CH_3COOH$, malic acid and mixtures thereof. In a preferred embodiment the acid is selected from the group consisting of HCl and $0.5H_2SO_4$, more preferably $0.5H_2SO_4$. By $0.5H_2SO_4$ it is meant that about half the molar amount of the pyrazole starting material is reacted to achieve the precipitation of the hemisulfate salt.

In order to reach the compound (IX) an alternative to the steps (e)+(f) describe above would be step (g); i.e. to treat the intermediate (I) via basic treatment. Step (g) is described hereafter:

VII. The Seventh Step g) Consists of the Formation of 4,5-amino-1-alkyl-1H-pyrazole-HZ (IX) Via a Basic Treatment of Intermediate (I) in the Presence of a Reducing Agent and a Base, Followed by Acid Treatment with an Acid HZ'

(g) Synthesizing 4,5-amino-1-alkyl-1H-pyrazole (IX)

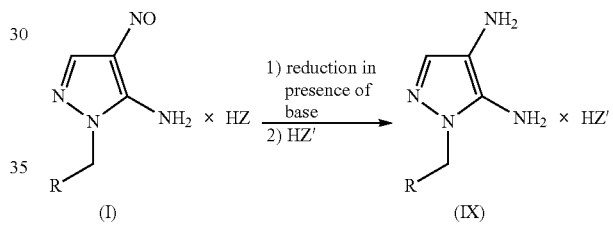

Non limiting examples of solvents for the step g) comprise pentane, 1,2-dimethoxyethane, cyclopentane, hexane, cyclohexane, benzene, toluene, 1,4-dioxane, diethyl ether, tetrahydrofuran, methyl-tetrahydrofuran, n-butanol, isopropanol, n-propanol, ethanol, methanol and mixtures thereof. In a preferred embodiment the solvent is selected from the group consisting of water and methanol and mixtures thereof.

Non limiting examples of a reducing agent for the reducing step 1) of step f) comprise hydrogen source such as Hydrazine, $H_2$ with a metal catalyst selected from the group consisting of Fe, Pd/C, Pd/(OH)$_2$, Raney-Ni, PtO$_2$ and mixtures thereof. In a preferred embodiment the reducing agent is $H_2$ with a Pd/C catalyst.

Non limiting examples of bases for the reducing step 1) of step g) comprise ammonia, alcoholates such as sodium methylate, potassium methylate, lithium methylate, alcali or earthalkali hydrxydes such as sodium hydroxide, potassium hydroxide, ammonium hydroxide, calcium hydroxide, magnesium hydroxide, barium hydroxide, aluminum hydroxide, ferrous hydroxide or Iron (II) hydroxide, ferric hydroxide or Iron (III) hydroxide, zinc hydroxide, lithium hydroxide, sodium bicarbonate, sodium acetate, potassium acetate, lithium acetate, ammonium acetate, sodium tert-butylate, potassium tert-butylate and mixtures thereof. The preferred base may be selected from sodium acetate, triethylamine or diisopropylethylamine.

Non limiting examples of acid HZ' for the step 2) of step g) comprise HCl, $H_2SO_4$, $0.5H_2SO_4$, $H_3PO_4$, $CH_3COOH$, malic acid and mixtures thereof. In a preferred embodiment the acid is selected from the group consisting of HCl, $0.5H_2SO_4$, more preferably $0.5H_2SO_4$.

VIII. Example

Application of the Telescoping One-Pot Reaction Process to the Total Synthesis of 5-amino-4-nitroso-1-n-hexyl-1H-pyrazole-HCl (I-a)

The following are non-limiting examples of the processes and compositions of the present invention. The examples are given solely for the purpose of illustration and are not to be construed as limitations of the present invention, as many variations thereof are possible without departing from the spirit and scope of the invention, which would be recognized by one of ordinary skill in the art. All concentrations are listed as weight percent, unless otherwise specified.

The process described above can be utilized to synthesize 5-amino-4-nitroso-1-n-hexyl-pyrazole-HCl formula (I-a). In one The telescoping process comprises the steps of:

(a) Synthesizing 3-hydrazinylpropanenitrile (IV)

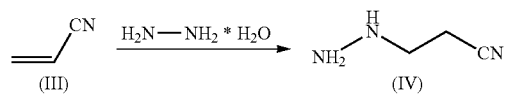

(b) Synthesizing 3-(2-hexylidenehydrazinyl)propanenitrile (VI-a)

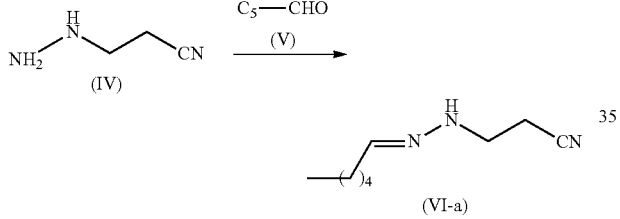

(c) Synthesizing 5-amino-1-n-hexyl-1H-pyrazole (VII-a)

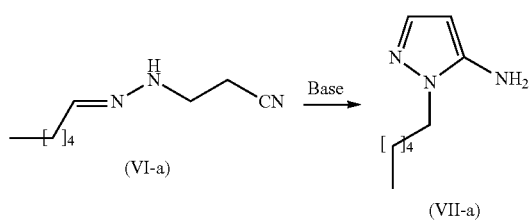

(d) Synthesizing 5-amino-4-nitroso-1-n-hexyl-1H-pyrazole-HCl (I-a)

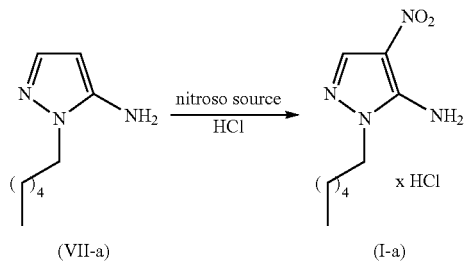

Non-limiting examples of subsequent reactions on compound (I-a) can be:

(e) Synthesizing 5-amino-4-nitroso-1-n-hexyl-1H-pyrazole (VIII-a)

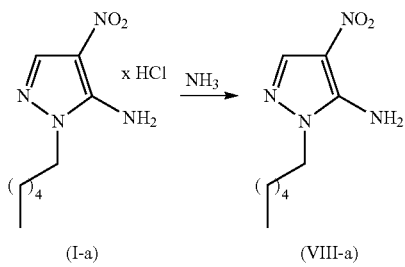

(f) Synthesizing 4,5-diamino-1-n-hexyl-1H-pyrazole Hemisulfate Salt (IX-a)

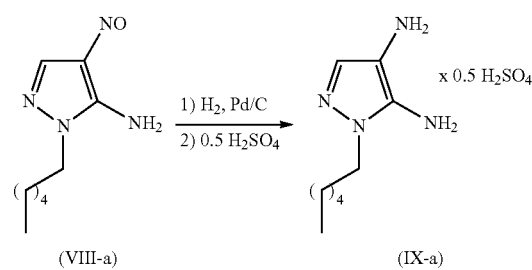

As an alternative to the subsequent reactions (e)+(f), the reaction on compound (I-a) can be:

(g) Synthesizing 4,5-diamino-1-n-hexyl-1H-pyrazole (IX-a)

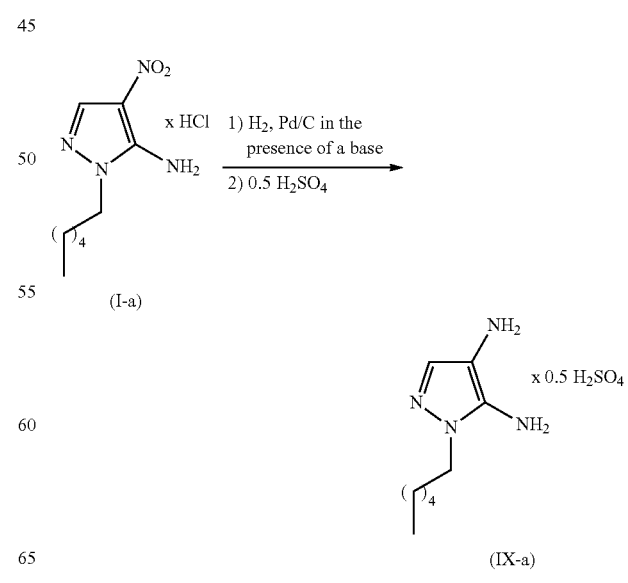

These examples will now be detailed hereinbelow.

Steps (a), (b), (c) and (d): Synthesis of 5-amino-4-nitroso-1-n-hexyl-1H-pyrazole×HCl (I-a)

| | | |
|---|---|---|
| | | To a 0° C. cold solution of |
| 5.1 | kg | hydrazine hydrate diluted with |
| 10.2 | l | propyl alcohol are continuously added at approx. 0° C. |
| 5.67 | kg | Acrylonitrile was added with control of the temperature. After the addition the reaction mixture is further stirred for a while at 0° C., then heated to room temperature and additionally stirred further for 30 min. Immediately afterwards |
| 10.7 | kg | hexanal are continuously added at room temperature with control of the temperature. After finishing the addition of hexanal the reaction mixture is stirred awhile and then reduced to dryness under vacuum. The residual liquid residue is diluted one after another with |
| 15.3 | l | propyl alcohol and |
| 1.70 | l | methanol and then heated to reflux. Under reflux and with intensive stirring a prepared solution of |
| 2.20 | kg | sodium methoxide, 30% solution in methanol dissolved in |
| 1.70 | l | propyl alcohol is continuously added After the addition the reaction mixture is stirred further for a period of approx. 2 h. Thereafter the solution is cooled down to less than 0° C. and |
| 11.9 | kg | 3-methylbutyl nitrite is added under temperature control so that the reaction temperature is kept at less than 0° C. After that the cold solution is continuously added into a less than 0° C. cold solution of |
| 25.1 | kg | HCl conc. in |
| 57.9 | l | 1,2-dimethoxyethane with continuous cooling to keep the reaction temperature at less than 0° C. When finishing the addition the formed suspension is further stirred at less than 0° C. for 0.5 h and then isolated yielding 12.6 kg 5-amino-4-nitroso-1-n-hexyl-1H-pyrazole × HCl (I-a) |

A $^1$HNMR spectrum of this compound is shown in FIG. 1.

Step (e) Synthesis of 5-amino-4-nitroso-1-n-hexyl-1H-pyrazole (VIII-a)

| | | |
|---|---|---|
| 22.1 | kg | 5-amino-4-nitroso-1-n-hexyl-1H-pyrazole × HCl (I-a) are dissolved in |
| 66.3 | l | methanol and |
| 49.7 | l | water. At room temperature a solution of |
| 7.77 | kg | ammonia 25% in |
| 22.1 | l | water is added within 0.5 hr. After finishing the addition the formed suspension is cooled down to room temperature. After stirring at room temperature for awhile, the precipitate is isolated yielding 17.0 kg 5-amino-4-nitroso-1-n-hexyl-1H-pyrazole (VIII-a) |

Step (f) Synthesis of 4,5-diamino-1-n-hexyl-1H-pyrazole×0.5H$_2$SO$_4$ (IX-a) (Starting with 5-amino-4-nitroso-1-n-hexyl-1H-pyrazole (VIII-a) (Free Base))

| | | |
|---|---|---|
| | | The mixture of |
| 7.0 | kg | 5-amino-4-nitroso-1-n-hexyl-1H-pyrazole (VIII-a), |
| 0.07 | kg | catalyst Pd/C 10%, containing 50% water, and |
| 1.4 | kg | activated carbon, suspended in |
| 21.0 | l | ethanol is hydrogenated at 60-80° C. under a pressure of 2-3 bar abs. When the reaction is finished, the solution is cooled to room temperature and filtered. The filter residue is washed twice with |
| 5.6 | l | ethanol in each case. The obtained filtrate and the washing liquids are slowly added to a approx. 50° C. warm solution of |
| 2.27 | kg | sulphuric acid conc. in |
| 16.8 | l | water and |
| 7.0 | l | ethanol. The addition is done at 50-55° C. During the addition the desired product precipitates. When the addition is finished the suspension is cooled down to 0-3° C., stirred further for approx. 30 min at the same temperature and filtered yielding 8.26 kg 4,5-diamino-1-n-hexyl-1H-pyrazole × 0.5 H$_2$SO$_4$ (IX-a) |

Figure 2:
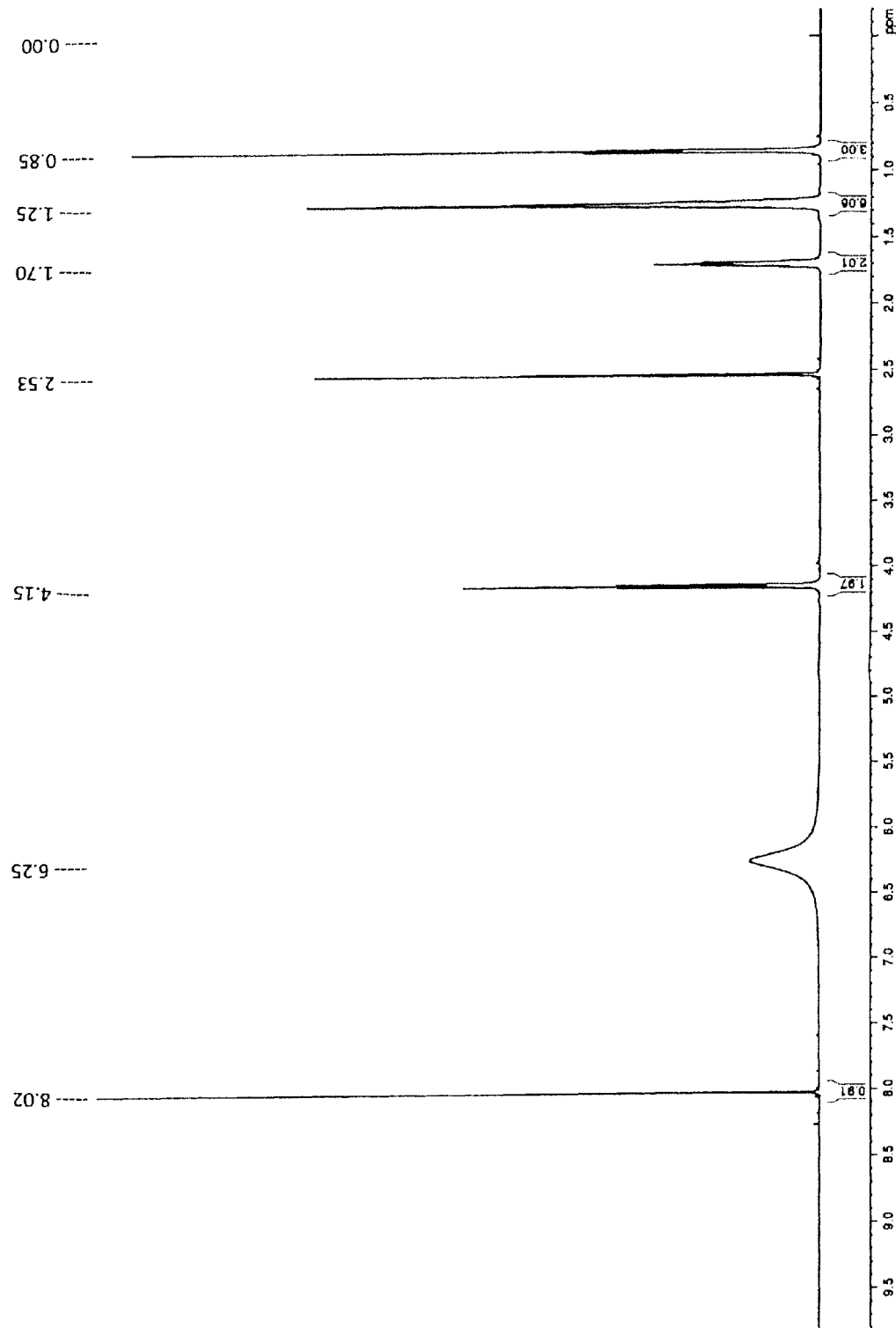
FIG. 2 is $^1$H NMR of 4,5-amino-1-n-hexyl-1H-pyrazole hemisulfate (herein IX-a)

A $^1$HNMR spectrum of this compound is shown in FIG. 2.

Step (g): Synthesis of 4,5-amino-1-n-hexyl-pyrazole Hemisulfate

Direct Reduction of (I-a) to (IX-a) with Use of Sodium Acetate

| | | |
|---|---|---|
| 40.0 | g | 5-amino-4-nitroso-1-n-hexyl-1H-pyrazole × HCl (I-a) are suspended in |
| 120 | ml | ethanol. With intensive stirring |
| 15.5 | g | sodium acetate are continuously added. The suspension was stirred for a while before |
| 0.4 | g | catalyst Pd/C 10% are added under an inert atmosphere. Afterwards the reaction mixture is hydrogenated at 50-70° C. under a hydrogen pressure of approx. 3 bar. When the hydrogenation has finished the reaction mixture is filtered. The filter residue is washed twice with |
| 32 | ml | ethanol. The filtrate and the washing liquid are continuously added into a warm (50-60° C.) solution of |
| 10.9 | g | sulfuric acid conc. in |
| 96 | ml | water and |
| 32 | ml | ethanol over a period of 30 min. After finishing the addition the formed suspension is cooled down to 0-5° C. After stirring at 0-5° C. for a while, the precipitate is isolated yielding 35.4 g of 4,5-diamino-1-n-hexyl-1H-pyrazole hemisulfate (IX-a) |

Step (g'): Synthesis of 4,5-amino-1-n-hexyl-1H-pyrazole Hemisulfate

Direct Reduction of (I-a) to (IX-a) with Use of Triethylamine

| | | |
|---|---|---|
| 30.0 | g | 5-amino-4-nitroso-1-n-hexyl-1H-pyrazole × HCl are suspended in |
| 60 | ml | ethanol. With intensive stirring |
| 13.7 | g | triethylamine are continuously added. The suspension was stirred for a while before |
| 0.3 | g | catalyst Pd/C 10%, suspended in |
| 30 | ml | ethanol, are added under an inert atmosphere. Afterwards the reaction mixture is hydrogenated at 50-70° C. under a hydrogen pressure of approx. 3 bar. When the hydrogenation has finished the reaction mixture is filtered. The filter residue is washed twice with |
| 22 | ml | ethanol. The filtrate and the washing liquid are continuously added into a warm (50-60° C.) solution of |
| 8.85 | g | sulfuric acid conc. in |
| 72 | ml | water and |
| 33 | ml | ethanol over a period of 30 min. After finishing the addition the formed suspension is cooled down to 0-5° C. After stirring at 0-5° C. for a while, the precipitate is isolated yielding 23.7 g of 4,5-diamino-1-n-hexyl-1H-pyrazole hemisulfate (IX-a). |

Concluding Remark

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Any embodiment disclosed as "preferred" is not intended as limiting the scope of protection, unless expressly mentioned otherwise.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A telescoping process for synthesizing 5-amino-4-nitroso-1-alkyl-1H-pyrazole salt (I), the process comprising the steps of:

a) synthesizing the intermediate 3-hydrazinylpropanenitrile (IV) via a 1,4 Michael addition using acrylonitrile (III) and hydrazine hydrate;

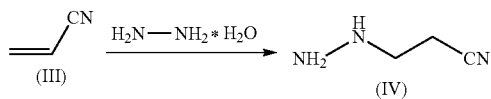

b) synthesizing the intermediate 3-(2-alkylidenehydrazinyl)propanenitrile (VI) via a condensation with intermediate (IV) and aldehyde (V):

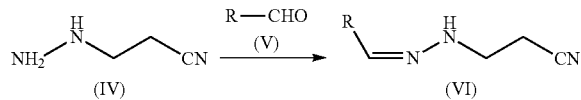

wherein R is a mono- or poly-substituted or unsubstituted, straight or branched, saturated or mono- or poly-unsaturated alkyl group;

c) synthesizing the intermediate 5-amino-1-alkyl-1H-pyrazole (VII) via a cyclisation with intermediate (VI) in the presence of a base;

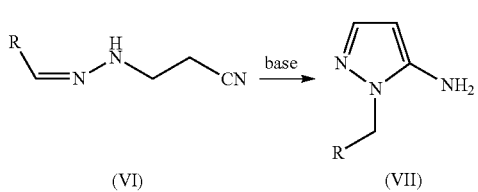

d) synthesizing 5-amino-4-nitroso-1-alkyl-1H-pyrazole salt (I) via a nitrosation step with intermediate (VII) in the presence of an acid HZ;

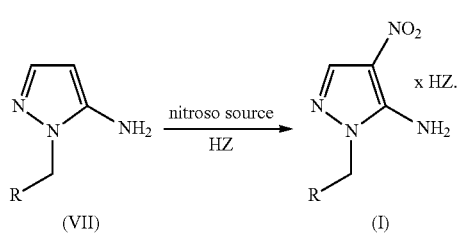

2. A telescoping process according to claim 1 wherein R is a C1-C11 straight unsubstituted alkyl group.

3. A telescoping process according to claim 2, wherein R is a C3-C7 straight unsubstituted alkyl group.

4. A telescoping process according to claim 3, wherein R is pentyl.

5. A telescoping process according to claim 1, wherein the base for step c) is selected from the group consisting of sodium methylate, potassium methylate, lithium methylate, sodium hydroxide, potassium hydroxide, ammonium hydroxide, calcium hydroxide, magnesium hydroxide, barium hydroxide, aluminum hydroxide, ferrous hydroxide or hydroxide, ferric hydroxide or Iron (III) hydroxide, zinc hydroxide, lithium hydroxide, sodium bicarbonate, sodium tert-butylate, potassium tert-butylate and mixtures thereof.

6. A telescoping process according to claim 5 wherein the base for step c) is selected from the group consisting of sodium methylate, potassium methylate and lithium methylate.

7. A telescoping process according to claim 1, wherein the acid HZ for step d) is HCl.

8. A telescoping process according to claim 1, wherein the nitroso source for step d) is selected from the group consisting of 3-methylbutyl nitrite, nitrosylsulfonic acid, tert-butylnitrite, butylnitrite and mixtures thereof.

9. A telescopic process according to claim 8 wherein the nitroso source is 3-methylbutyl nitrite.

10. A telescopic process according to claim 1 for synthesizing 5-amino-4-nitroso-1-n-hexyl-pyrazole-HCl (I-a), wherein said process comprises the steps of:

a) synthesizing 3-hydrazinylpropanenitrile (IV):

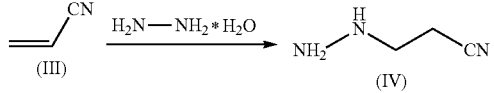

b) synthesizing 3-(2-hexylidenehydrazinyl)propanenitrile (VI-a):

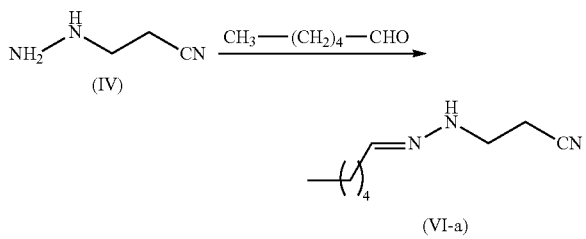

c) synthesizing 5-amino-1-n-hexyl-pyrazole (VII-a):

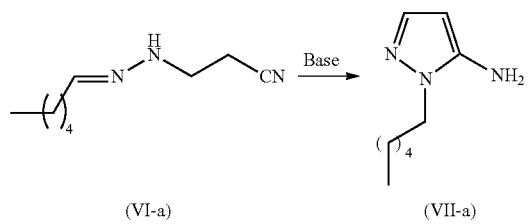

d) synthesizing 5-amino-4-nitroso-1-n-hexyl-pyrazole-HCl (I-a):

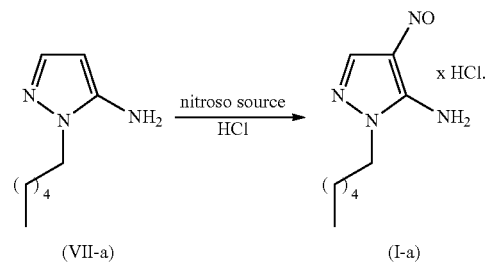

* * * * *